(12) United States Patent
Del Prete et al.

(10) Patent No.: US 8,455,462 B2
(45) Date of Patent: Jun. 4, 2013

(54) OPHTHALMIC COMPOSITIONS BASED ON TAMARIND SEED POLYSACCHARIDE AND HYALURONIC ACID

(75) Inventors: Antonio Del Prete, Naples (IT); Marco Sanso, Milan (IT)

(73) Assignee: RMFA Trading S.A., Lugano-Paradiso (CH)

( * ) Notice: Subject to any disclaimer, the term of this patent is extended or adjusted under 35 U.S.C. 154(b) by 207 days.

(21) Appl. No.: 12/681,256

(22) PCT Filed: Oct. 2, 2008

(86) PCT No.: PCT/IT2008/000626
§ 371 (c)(1),
(2), (4) Date: Jun. 18, 2010

(87) PCT Pub. No.: WO2009/044423
PCT Pub. Date: Apr. 9, 2009

(65) Prior Publication Data
US 2010/0279981 A1    Nov. 4, 2010

(30) Foreign Application Priority Data
Oct. 2, 2007   (IT) .............................. RM2007A0510

(51) Int. Cl.
| | |
|---|---|
| *A01N 43/04* | (2006.01) |
| *A61K 31/715* | (2006.01) |
| *C07H 3/00* | (2006.01) |
| *C07H 1/00* | (2006.01) |
| *C08B 37/00* | (2006.01) |
| *C08B 37/06* | (2006.01) |
| *C12P 19/04* | (2006.01) |

(52) U.S. Cl.
USPC .................................. 514/54; 536/2; 536/123

(58) Field of Classification Search
None
See application file for complete search history.

(56) References Cited

U.S. PATENT DOCUMENTS
5,106,615 A * 4/1992 Dikstein .................... 424/78.04
2006/0222623 A1 * 10/2006 Xia et al. ................... 424/78.38

FOREIGN PATENT DOCUMENTS
WO    WO 97/28787 A    8/1997
WO    WO 2006/085351 A    8/2006

OTHER PUBLICATIONS

M. J. O'Neil et al. (I), "The Merck Index, 14th Edition," Merck & Co., Whitehouse Station, NJ, 2006, only pp. 822-823 supplied (see "Hyaluronic Acid").*
M. J. O'Neil et al. (II), "The Merck Index, 14th Edition," Merck & Co., Whitehouse Station, NJ, 2006, only p. 1554 supplied (see "Tamarind").*
M. J. O'Neil et al. (III), "The Merck Index, 14th Edition," Merck & Co., Whitehouse Station, NJ, 2006, only p. 1218 supplied (see "Pectin").*
Mullins et al., "Ophthalmic Preparations," Chapter 86 in Remington's Pharmaceutical Sciences, 18th Edition, Gennaro et al (eds.), Mack Publishing Co., Easton, PA, 1990, only pp. 1581-1595 supplied.*
Rolando Maurizio et al.: Establishing the Tolerability and Performance of Tamarind Seed Polysaccharide (TSP) in Treating Dry Eye Syndrome: Results of a Clinical Study, Mar. 29, 2007, vol. 7, No. 1, BMC Ophthalmology, Biomed Central, London, GB.
Burgalassi S et al.: Development of a Simple Dry Eye Model in the Albino Rabbit and Evaluation of Some Tear Substitutes, Jan. 1, 1999, vol. 31, No. 3, Ophthalmic Research, Basel, CH.

* cited by examiner

*Primary Examiner* — Lawrence E Crane
(74) *Attorney, Agent, or Firm* — Arent Fox LLP (57) ABSTRACT

The invention concerns ophthalmic solutions indicated for use as tear substitutes, containing a combination of hyaluronic acid and a polysaccharide known as TSP (*Tamarindus indica* Seed Polisaccharide) which are able, when administered together in a combination, to act synergistically in stimulating the return to normality of the conjunctival mucosa affected by dry eye syndrome, thus inducing a remarkable improvement in the number and morphology of the conjunctival microvilli.

The ophthalmic preparations, proposed for use in the treatment of dry eye syndrome contain, in combination, from 0.05 to 2% by weight of tamarind seed polysaccharide (TSP) and from 0.05 to 1% by weight of hyaluronic acid in aqueous solution.

15 Claims, 6 Drawing Sheets

OPHTHALMIC COMPOSITIONS BASED ON TAMARIND SEED POLYSACCHARIDE AND HYALURONIC ACID

CROSS-REFERENCED TO RELATED APPLICATIONS

This application is a National Stage entry of International Application No. PCT/IT2008/000626, filed Oct. 2, 2008, which claims priority to Italian Patent Application No. RM2007A000510, filed Oct. 2, 2007. The prior applications are herein incorporated by reference in their entirety.

DESCRIPTION

The present invention concerns ophthalmic compositions based on tamarind seed polysaccharide and hyaluronic acid. More particularly, the invention concerns ophthalmic solutions indicated for use as tear substitutes, containing a combination of hyaluronic acid and a polysaccharide known as TSP (*Tamarindus indica* Seed Polisaccharide) which are able, when administered together in a combination, to act synergistically in stimulating the return to normality in the conjunctival mucosa affected by the dry eye syndrome, thus inducing a remarkable improvement in the number and morphology of the conjunctival microvilli.

As it is known, the eye surface is maintained constantly humid by the presence of the pre-corneal tear film, which is an organized liquid structure coating the conjunctiva and the exposed surface of the eyeball. It is fundamentally important that the structure is quantitatively and qualitatively suitable in order to obtain proper cleansing and protection. In addition, the tear film contains substances with high bactericide power as lysozyme and antibodies, which protect the eyes from the attack of many antigens.

In normal conditions, the tears, which are the result of a series of solutions excreted by different glands in the conjunctival sac, are arranged in layers over the corneal and conjunctival surface by the eyelids movements, thereby making up a complex three-layered structure, comprising:

- an internal layer of mucus, consisting of a mixture of glycoproteins (mucin) produced by specialized cells (i.e. the conjunctival goblet cells) which are present in the conjunctival epithelium—said layer is adsorbed on the cornea, thus transforming the corneal epithelium in a hydrophilic surface: if mucin is lacking the epithelial cells are hydrophobic and cannot be hydrated by the tears;
- a thick intermediate aqueous layer (secreted by the main and accessory lachrymal glands) consisting essentially of water, electrolytes, proteins, enzymes and mucin; this layer is spread over the said hydrophilic surface, and has the function of providing atmospheric oxygen to the corneal epithelium, of exerting an antibacterial activity and of washing away any debris;
- a thin external lipid layer (secreted by sebaceus tarsal palpebral glands or Meibomian glands), having the following functions: retarding the underlying water layer evaporation, increasing the surface tension to stabilize the film avoiding its escape on the skin and lubricating the eyelids.

The eyelids movement squeezes the mucus out of the conjunctival cells and introduces it into the fornixes, and from there it is uniformly distributed on the whole corneal surface by the blinking movements of the eyes.

The three-layers structure described above constitutes a complex physiological system, having the main functions of protecting the eye surface, maintaining the hydration, the lubrication and the clearness of the corneal surface, and of cooperating in producing a correct vision. The perfect equilibrium and continuous renovation of the said physiological system is a necessary condition for it to be able to carry out said functions. For the said equilibrium and renovation to be realized, a constant but not excessive water evaporation from the tear fluid must take place, so as to keep the osmolarity thereof to the physiological level of about 300 mOsm/l, and the tear film must be continuously redistributed on the corneal surface as a result of the blinking.

Not only the layered structure of the different components is important, but also the solutes present therein are important. The lipids of the external layer are arranged into a double phase: a polar phase, adjacent to the intermediate layer, and a thicker phase at the interface with the air. The aqueous phase shows instead fixed ionic concentrations: mainly sodium, potassium, calcium, magnesium, zinc, chlorine and bicarbonate are important for maintaining the tears osmolarity.

The integrity of the internal mucin layer represents one of the essential elements of the maintenance of the tear film stability. This because mucin enhances the wettability of the corneal surface, allows the aqueous film to keep adhering to the exposed surface in a continuous and homogeneous way, thus safeguarding its stability, and increases the viscosity of the lachrymal fluid, preventing it from flowing away too rapidly from the conjunctival sac. As already noted, when mucin is absent or insufficient the cornea becomes non-wettable and, as a consequence of the unbalance between electrolytes and glycoproteins present, the tear film becomes unstable and subject to breaking, with formation of dry areas.

Various diseases or abnormal conditions of the eye manifest themselves with tear film discontinuities, as a result, e.g., of an insufficient blinking frequency, of the prolonged use of contact lenses, of the administration of some systemic drugs or, more frequently, of a senile hyposecretion. More frequently, the deterioration of the efficient lubricant and protective system described above appears in the "dry eye syndrome", the rate of which is greatly increasing, notably because of the atmospheric pollution and the consequent arising of new kind of allergies. Actually, the dry eye syndrome is the most frequent pathology in ophthalmology, whit a rate between 10 and 15% of the general population. In this connection, the term "dry eye" is commonly used to refer to the ophthalmic conditions resulting from the reduction or the instability of the tear film—characterized form a subjective point of view, by a series of annoying symptoms comprising burning sensation, foreign body sensation, photophobia and blurred vision, heavy ocular feeling, easy irritation due to wind, smoke and dusts and visual disturbances—while the typical alterations of the corneal surface occurring in this connection are generally referred to by the term "keratoconjunctivitis sicca".

In such situations a degeneration of the conjunctival cells occurs, resulting in increased desquamation, loss of the cell surface microplicae, breaking of the epithelial cells membrane and reduction of the number of mucin-producing goblet cells. The corneal and conjunctival epithelial cells appear to be suffering and with a reduced number of microvilli, until their complete disappearance. The reduction of the number of microvilli is with a good approximation proportional to the affection severity and to the seriousness of the symptomatology. This anatomo-pathological situation is accompanied, in various degrees, by an infiltration of inflammatory cells at the level of the conjunctival cells. (Cennamo G. L., Del Prete A., Forte R., Cafiero G-, Del Prete S., Marasco D., Impression cytology with scanning electron microscopy: a new method in the study of conjunctival microvilli, *Eye* (2007), 1-6).

Besides this, the dry eye syndrome, lacking a protective effect of the tear film, predisposes to other pathological conditions such as actinic, bacterial, viral and allergic keratoconjunctivitis.

As studies on human pathologies showed all the changes that occur in a dry eye, the preclinical study into an animal model of keratoconjunctivitis sicca helped to understand the natural cause of these changes. (Gilbard J. P., Rossi S. R., Gray K. L.: A new rabbit model for keratoconjunctivitis sicca, *Invest. Ophthalmol. Vis. Sci.* 28(2):225-228, (1987); Gilbard J. P., Rossi S. R., Gray K. L., Hanninen L. A.: Natural history of disease in a rabbit model for keratoconjunctivitis sicca, *Acta Ophthalmol.* (Suppl.) 192:95-101, (1989). It is now known that dry eye develops through four distinct phases:
  1. loss of water from the tear film with an increase of osmolarity of the film itself;
  2. decrease of the density of the globets cells and decrease of the corneal glycogen (energetic source for the healing of possible corneal lesions);
  3. increase of corneal desquamation (due to the increase of the osmotic gradient between tear film and the ocular surface, and to the decrease of the globet cells, which recall water from the epithelial cells of the conjunctiva);
  4. destabilization of the cornea-tear film interface.

From a diagnostic point of view, dry eye syndrome may be detected and monitored not only by means of the evaluation of the typical symptoms thereof, but also by means of well established procedures, including, as the most common, the evaluation of lachrymal secretion (Schirmer test), the evaluation of the time needed for the tear film to break after a compete blinking (break-up time, BUT), and the evaluation of the colour of the corneal surface upon staining with rose bengal or fluorescein.

Another phenomenon which is unanimously considered to be a sign of an irregularly structured tear film is the reduction of the mucus ferning. In normal conditions, mucus is characterized by crystallizing in a fern pattern when made to evaporate at room temperature from an aqueous solution. The ferning phenomenon, which is believed to result from the interaction of the electrolytes with the high molecular weight glycoproteins of mucus, is evidenced after a short time from the collection of tear mucus from the lower fornix of the conjunctiva. It has been ascertained that the various different patterns of said phenomenon, evidenced by the ferning test, (i.e., Type I, uniform ferning; Type II, good amount of ferning with ferns of reduced size and empty spaces; Type III; ferning only partially present, Type IV, ferning absent) are connected with the normal or pathological condition of the tear fluid. A dense ferning, for instance, is considered to be the expression of a perfect equilibrium between mucin and electrolytes, while the partial presence or the absence of tear ferning, which is detected in eyes affected by keratoconjunctivitis sicca, denotes a quantitative lack of tear mucus or a qualitative alteration of the glycoproteins or of their environment (i.e., pH, hydration, electrolytic equilibrium).

Keratoconjunctivitis sicca is normally treated with liquid ophthalmic preparations generally known as "artificial tears", to be instilled in drops in order to replace or supplement the natural tear production. In the simplest case said preparations have only a moistening effect, as they consist of physiological saline solutions, neutral and isotonic with the lachrymal film, based on sodium chloride only or on balanced mixtures of various electrolytes.

In order to overcome the drawback of the reduced retention inside the conjunctival sac, which is typical of such saline solutions, artificial tear preparations have been introduced, which are made viscous by the addition of high molecular weight agents, such as, usually, water-soluble polymers of a synthetic, semi-synthetic or natural origin. However, it has been found that, for said viscosity enhancers to confer advantageous features to a composition for use as artificial tear, it is not sufficient that said viscosity enhancers generically increase the viscosity of the product, but it is also necessary that the dispersions thus formed have properties as close as possible to those of mucin dispersions. Namely, said dispersions must behave as much as possible as mucomimetic substances. This requires, first of all, a particular rheological behaviour, i.e. non-newtonian, (specifically pseudoplastic) similar to the rheological behaviour of natural tears. In effect, only few of the macromolecular products that may be used as viscosifiers for artificial tears are actually able to show a similar behaviour.

Examples of compositions for use as artificial tears having non-newtonian rheologic behaviour are those containing carboxyvinyl polymers such as Carbopol®, the cellulose esters, such as methylcellulose and the alcoholic derivatives thereof, (e.g. hydroxypropylcellulose and hydroxypropylmethylcellulose) and hyaluronic acid. The latter is a polysaccharide of natural origin present in many tissues and fluids, both human and animal, and largely employed in ophthalmic preparations, owing to the marked pseudoplastic behaviour of its aqueous solutions, and because of its good capacity to link both with water and the epithelial cell wall.

A natural polysaccharide polymer that may be considered enclosed in the cited category is the polysaccharide obtained from seeds of the tamarind tree, the *Tanarindus indica*, an evergreen plant that may reach 15 m of height and that produces legume fruit and that is widespread in India, in Africa and the whole the Far East where it is cultivated primarily for food production. The fruit contains big seeds having an high percentage of polysaccharides, which have the function to accumulate and preserve vital energetic substances.

The seed, which was considered originally a by-product, has found various applications, once ground to the powder form (known as "tamarind gum" or "tamarind kernel powder"). The most important of such applications are in textile industry and in paper industry, where tamarind gum is employed respectively as sizing agent, and in food industry, where it is used as thickening, gelling, stabilizing and binding agent in any kind of products, as do other polysaccharide products such as alginates, pectines, guar gum or locust bean gum. Raw tamarind kernel powder, which is commercially available as such, contains from 65 to 73% by weight of polysaccharide, from 15 to 23% of protein material, from 3 to 8% of fats and oil and from 2 to 4% of ashes, besides minor amounts of crude fibre, tannins and other impurities.

In the pharmaceutical field, the polysaccharide fraction of tamarind gum (tamarind seed polysaccharide, in the following also referred to as TSP) has found a valid use as active component of tear substitutes and as carrier for topical ophthalmic sustained release drugs as described, in particular, in the European Patent EP 0892636 (Farmigea) and in the corresponding U.S. Pat. No. 6,056,950, the contents of which is incorporated herein by reference. Among the mucomimetic properties that the polysaccharide fraction of tamarind gum appears to have it must be evidenced the "ferning" ability previously described. Therefore, similarly to the hyaluronic acid, said polysaccharide fraction is able to give, by evaporation, crystalline products having morphology quite similar to that of crystallized tear mucus.

In view of the foregoing, an object of the present invention is to define a pharmacologic treatment for the dry eye syndrome therapy wherein the tear substitute is not only able to remain for a long time on the ocular surface and to self-integrate with the surface of the epithelia, exerting a protective role over them, but also is able to help the restoration of their integrity, particularly to help a rapid return to normality in the conjunctival mucosa, overall in respect of the number and of the morphology of the microvilli.

In the frame of the studies that lead to the invention it was considered that both the known ophthalmic solutions based on TSP and those more widely diffused based on hyaluronic acid showed to be able to produce an improvement in the symptomatology of the dry eye, improvement that is at the base of their marketing success in the treatment of this disease, but both such solutions produced relatively modest benefits as concerns an effectiveness and rapid recovery from the histological damages that are typical of the considered pathology, particularly in regard of the microscopic surface structure of the conjunctival epithelium.

On the basis of the previous considerations it has been found, according to the present invention, that the specific combination of the active ingredients TSP and hyaluronic acid, applied on the ocular surface in a single ophthalmic product, acquires new therapeutical properties that the two products taken separately do not have, particularly in helping a more rapid return to normality of the conjunctival mucosa, especially in regard of the number and morphology of the microvilli. The restoration of the normal integrity of the microvilli is associated with a longer lasting effect on the improvement of the signs and symptoms that accompany the dry eye syndrome.

According to several studies carried out on the structure of the polysaccharide fraction of tamarind gum, it is ascertained that tamarind seed polysaccharide consists of a main chain of glucopyranosyl units bound to each other through (1→4) linkages, with short side chains consisting of xylopyranosyl units attached to the main chain through (1→6) linkages. Said xylopyranosyl units are single, or they may be bound, in turn, to single galactopyranosyl units through a (1→2) linkage. It was also reported the further presence of arabinofuranosyl units. Therefore, the structure of the tamarind seed polysaccharide (TSP) may be represented as follows The procedure for the extraction, filtration and purification of the polymer from the starting raw material requires a high technological specialization in order to maintain unchanged the functional characteristics, also in view of the high molecular weight, which ranges, in a correctly purified product, from 600,000 to 750,000 Da.

The hyaluronic acid is chemically definable as an unbranched glycosaminoglycan, consisting of alternate units of D-glucuronic acid (GlcUA) and N-acetyl-D-glucosamine (GlcNAc), which structure may be represented by the following formula:

which shows two distinct disaccharide units in sequence, and wherein the number n of the repeating couples of units is such that the molecular weight of the polysaccharide is comprised between 50,000 and several millions of dalton. The average molecular weight of the hyaluronic acid used in ophthalmology (in the form of the corresponding sodium salt) for artificial tear solutions is normally comprised between 700,000 and 1 million Da.

In vivo, all the carboxyl groups of the hyaluronic acid and of N-acetylglucosamine are completely ionized, conferring high polarity to the hyaluronic acid molecule and consequently high solubility in water. By virtue of its good ability of linking both with water and with the epithelium cell wall, hyaluronic acid is used as the main component in many tear substitutes in the treatment of the dry eye pathology.

In the field of the studies connected to the present invention, some laboratory tests based on the employment of magnetic resonance techniques (which will be described in detail below) showed that TSP is able to interact in solution with the hyaluronic acid (HA) inducing conformational changes that mainly interest the internal glucose and galactose units of TSP and the acetyl groups of HA. This fact produces effect on the ability of the admixture to retain water that, for some concentration ratios, turns out to be remarkably higher than shown by the two polymers in non-mixed form.

Because the ability to retain water is fundamental for the adhesive and biocompatibility characteristics of a polymer to be used for the dry eye treatment, the research on the TSP-HA mixture has been further extended, by means of preclinical tests over a dry eye model induced in rat with atropine, in order to evaluate the safety and the tolerability of the mixture. On the basis of the results obtained on such model (also synthetically reported in the following) it is possible to confirm that the mixture of TSP and HA does not show negative interactions between the two products and that it promotes a better recovering of the histo-physiologic damages subsequent to an acute reduction of tear production.

A subsequent clinical test carried out as a pilot study on a relatively limited number of patients (reported in the following) has confirmed the effectiveness of the proposed treatment, pointing out a remarkable synergic effect of the combination of TSP and HA.

Therefore, the present invention specifically provides an ophthalmic preparation for use as tear substitute containing, in combination, from 0.05 to 2% by weight of tamarind seed polysaccharide and from 0.05 to 1% by weight of hyaluronic acid in aqueous solution.

The term "tamarind seed polysaccharide" (*Tamarindus indica* Seed Polysaccharide or TSP, sometimes also generically referred to with the term "xyloglucan") as used in the present application, means any polysaccharide-enriched fraction obtainable from tamarind gum (i.e. tamarind kernel powder), the latter being the raw product currently available on the market. A partially purified polysaccharide fraction of tamarind gum is sold, for instance, by Dainippon Pharmaceutical Co. LTD of Osaka, Japan, under the trade name Glyloid®. For the purpose of the present invention, however, the concerned polysaccharide fraction is preferably further purified to give a practically pure tamarind seed polysaccharide.

The term "hyaluronic acid", as used in the present application, means the previously described polysaccharide (generally also referred to as "glycosaminoglycan"), in particular in the salt form commonly used for the formulation of artificial tears, i.e. sodium hyaluronate.

Preferably, the ophthalmic preparation according to the invention contains, in combination in aqueous solution, from 0.1 to 1% by weight of tamarind seed polysaccharide and from 0.1 to 0.5% by weight of hyaluronic acid.

Preferably, the weight concentrations in the ophthalmic preparation according to the invention are comprised between 0.1 and 1% of tamarind seed polysaccharide and between 0.1 and 0.5% by weight of hyaluronic acid. An embodiment which has been specifically studied in the experimental work provided below, and which provides superior clinical performances regarding the ability of the two active agents to cooperate in restoring the normality of the conjunctival epithelium, contains, in aqueous solution, 0.2% by weight of tamarind seed polysaccharide and 0.4% by weight of hyaluronic acid.

Preferably, the tamarind seed polysaccharide used in the preparations of the invention has a molecular weight comprised in the range from 450,000 Da to 750,000 Da (preferably 600,000-750,000 Da), and the hyaluronic acid has molecular weight comprised in the range from 600,000 Da to 1,000,000 Da (preferably 700,000-1,000,000 Da).

In the artificial tear formulations according to the invention one or more tonicity adjusting agents should be added, so as to give the solution a correct value of osmolarity. To this aim, any one of the products currently employed in the art as tonicity agents may be used, such as, for instance, sodium chloride, potassium chloride, mannitol, dextrose, boric acid, sorbitol or propylene glycol.

Other ingredients which may be included in the formulation, in accordance with the known art, are acids or bases as pH adjusting agents, as well as buffers, such as, e.g., the phosphate buffer (monobasic sodium phosphate and dibasic sodium phosphate), or acetate buffer (acetate—acetic acid system). Other buffers that may be used are the borate, citrate, bicarbonate and trizma (tri-hydroxymethyl-aminomethane) buffers.

The composition may also comprise preservatives and antimicrobial agents, such as benzalkonium chloride, sodium merthiolate or thimerosal, methyl-, ethyl- and propyl paraben, chlorobutanol, phenilmercurium nitrate or acetate, phenylethyl alcohol, chlorhexidine acetate or giuconate, as well as chelating agents such as the edetates or EDTA. Owing to the problems of tolerability of the preservatives, it is preferred not to include such ingredients in the formulations for use as artificial tears. This is clearly possible when the product is packaged in unit-dose containers. In some cases, however, and specially when the product is in multiple dose containers, the addition of preservatives is necessary.

According to a further aspect thereof, the present invention concerns the use of a combination of tamarind seed polysaccharide and of hyaluronic acid in aqueous solution for the production of a preparation for the treatment of dry eye syndrome.

As already noted, said tear substitute or preparation preferably comprises from 0.05 to 2% by weight of tamarind seed polysaccharide and from 0.05 to 1% by weight of hyaluronic acid, and more preferably it comprises from 0.1 to 1% by weight of tamarind seed polysaccharide and from 0.1 to 0.5% by weight of hyaluronic acid.

The tamarind seed polysaccharide of the proposed preparation for the use described below suitably has a molecular weight comprised from 600,000 Da to 750,000 Da, while the molecular weight of hyaluronic acid is preferably comprised from 700,000 Da to 1,000,000 Da.

The present invention is also disclosed by the following non-limiting examples, according to some specific embodiments thereof, which illustrate examples of formulations based on xyloglucan and hyaluronic acid employed as tears substitutes, having a protective and re-epithelizing activity, according to what is experimentally ascertained and reported in the experimental statement that follows.

EXAMPLES OF ARTIFICIAL TEARS FORMULATIONS

Example 1

| Ingredients | % by weight |
| --- | --- |
| TSP | 0.1 |
| Hyaluronic Acid | 0.1 |
| Mannitol | 2.00 |
| Deionised water | q.s. to 100 |
| Monobasic sodium and dibasic sodium phosphate | q.s. to pH 7.0 ± 0.5 |

The product is prepared by the following steps:
TSP and HA are weighted into a suitable glass vessel;
90% of the available water is added with a light stirring until complete dissolution of the product;
The mannitol amount is added, keeping stirring, and the mixture is left under stirring until complete dissolution of the product;
Deionized water is added up to the final weight (100%);
monobasic sodium and dibasic sodium phosphate are added to reach desired pH;
the solution so obtained is sterilized in autoclave or, in alternative, sterilized by filtration with a 0.22 micron filter.

Example 2

| Ingredients | % by weight |
| --- | --- |
| TSP | 0.1 |
| Hyaluronic Acid | 0.4 |
| Mannitol | 2.00 |
| Deionised water | q.s. to 100 |

-continued

| Ingredients | % by weight |
| --- | --- |
| Monobasic sodium and dibasic sodium phosphate | q.s. to pH 7.0 ± 0.5 |

The product is prepared in the same way as in the example 1.

Example 3

| Ingredients | % by weight |
| --- | --- |
| TSP | 0.2 |
| Hyaluronic Acid | 0.1 |
| mannitol | 2.00 |
| Deionised water | q.s. to 100 |
| Monobasic sodium and dibasic sodium phosphate | q.s. for pH 7.0 ± 0.5 |

The product is prepared in the same way as in the example 1.

Example 4

| Ingredients | % by weight |
| --- | --- |
| TSP | 0.2 |
| Hyaluronic Acid | 0.2 |
| Mannitol | 2.00 |
| Deionised water | q.s. to 100 |
| Monobasic sodium and dibasic sodium phosphate | q.s. to pH 7.0 ± 0.5 |

The product is prepared in the same way as in the example 1.

Example 5

| Ingredients | % by weight |
| --- | --- |
| TSP | 0.2 |
| Hyaluronic Acid | 0.4 |
| Mannitol | 2.00 |
| Deionised water | q.s. to 100 |
| Monobasic sodium and dibasic sodium phosphate | q.s. to pH 7.0 ± 0.5 |

The product is prepared in the same way as in the example 1.

Example 6

| Ingredients | % by weight |
| --- | --- |
| TSP | 0.4 |
| Hyaluronic Acid | 0.1 |
| Mannitol | 2.00 |
| Deionised water | q.s. to 100 |

-continued

| Ingredients | % by weight |
| --- | --- |
| Monobasic sodium and dibasic sodium phosphate | q.s. to pH 7.0 ± 0.5 |

The product is prepared in the same way as in the example 1.

Example 7

| Ingredients | % by weight |
| --- | --- |
| TSP | 0.4 |
| Hyaluronic Acid | 0.2 |
| Mannitol | 2.00 |
| Deionised water | q.s. to 100 |
| Monobasic sodium and dibasic sodium phosphate | q.s. to pH 7.0 ± 0.5 |

The product is prepared in the same way as in the example 1.

Example 8

| Ingredients | % by weight |
| --- | --- |
| TSP | 1.0 |
| Hyaluronic Acid | 0.1 |
| Mannitol | 2.00 |
| Deionised water | q.s. to 100 |
| Monobasic sodium and dibasic sodium phosphate | q.s. to pH 7.0 ± 0.5 |

The product is prepared in the same way as in the example 1.

Example 9

| Ingredients | % by weight |
| --- | --- |
| TSP | 1.0 |
| Hyaluronic Acid | 0.4 |
| Mannitol | 2.00 |
| Deionised water | q.s. to 100 |
| Monobasic sodium and dibasic sodium phosphate | q.s. to pH 7.0 ± 0.5 |

The product is prepared in the same way as in the example 1.

Some experimental results showing the features of the polysaccharide combinations according to the invention and the performance of the preparations containing the same are given below, together with some graphs and photographs shown in the accompanying drawings, wherein.

NMR Research on Hyaluronic Acid (HA) and TSP Mixture On Aqueous Solution

The polysaccharide hydrogels are provided of a very complicated tri-dimensional structure, within which water may be incorporated. The water content, the type of interaction that occurs between water and the polymer materials, as well as the water distribution internally to the polymer itself have a critic influence on the mechanical properties, the muco-adhesivity and are at the base of the high degree of biocompatibility. Commonly three types of water are distinguished in the polysaccharide gel: linked water, intermediate water and free water.

The Nuclear Magnetic Resonance spectroscopy (NMR) represents one of the most useful techniques for the study of the structure, the mobility and the hydration properties of the polymeric systems. In particular, very useful appears the measurement of the relaxation time spin-spin ($T_2$) or spin-grid ($T_1$) of the water protons nuclei. The relaxation time $T_2$ represents the constant time which describes the decay of the transversal magnetization in time, while the relaxation time $T_1$ describes the recovering process of the longitudinal magnetization.

When a polysaccharide is dissolved in water, the water molecules form hydrogen bonds with it and therefore their mobility is reduced, leading to a reduction of both $T_1$ and $T_2$. Commonly, however, distinct signals are not detected for the bonded water and the free water, but a single signal which represents the weighted average of the contributions deriving from the two kinds of water. As a consequence, the NMR parameter measured ($T_1$ and/or $T_2$) represents the weighted average of this parameter in the free and bonded status, according the following equation (equation 1):

$$\frac{1}{T_{obs}} = X_b \frac{1}{T_b} + X_f \frac{1}{T_f} \quad (1)$$

wherein $$\frac{1}{T_{obs}}$$

describes the relaxation speed rate (reciprocal of the time $T_1$ or $T_2$) measured for the water in the concerned solution, $$\frac{1}{T_b}$$

is the relaxation speed rate of the bonded water and $$\frac{1}{T_f}$$

is the relaxation speed rate of the free water, equal to the one measured into a solution lacking the polymeric material. $X_b$ and $X_f$ are, respectively, the molar fraction of the bonded and free water.

The number of bonded water molecules may be expressed in the following way, as dependant on the surface S of the polymer, on the thickness K of the bonded water superficial layer and on the total volume of water V (equation 2):

$$X_b = K \times \frac{S}{V} \quad (2)$$

When the polymer concentration increases, both $T_1$ and $T_2$ decrease as a consequence of the increasing of the polymer surface and, therefore, of the number of molecules of bonded water, unless conformational variations or self-regulating phenomena occur depending on the variation of the concentration itself; however, the effect on the transversal relaxation speed $$\left(\frac{1}{T_2}\right)$$

is much more marked than that noticed on the longitudinal relaxation speed $$\left(\frac{1}{T_1}\right).$$

On these grounds, the following experiments of measuring the transversal relaxation speed $$\left(\frac{1}{T_2}\right)$$

in the water proton nuclei were carried out in the following solutions:
a) TSP solutions having variable concentration, from 0.1% (w/w) to 1%;
b) HA solutions having variable concentration, from 0.1% (w/w) to 1%;
c) Mixtures containing variable concentrations of HA and TSP, with constant total concentration equal to 0.5%, obtained by mixing suitable volumes of mother solutions with total concentration of 0.5%;
d) Mixtures containing variable concentrations of HA and TSP, with constant total concentration equal to 1%, obtained by mixing suitable volumes of mother solutions with total concentration of 1%.

In order to obtain information on the nature of the interaction that occurs between the two polymeric materials, spectral parameters of the two polymers HA and TSP in the different concentrations and in their mixtures have been also compared. The spectral parameters considered are the following:
1. chemical shift of $^{23}$Na of HA;
2. relaxation measures of selective spin-grid on anomeric protons of TSP and on acetyl protons of HA;
3. relaxation measures spin-spin on protons of HA and TSP;
4. DOSY (Diffusion Ordered SpectrocsopY) measures for determining the diffusion of $H_2O$ (determination of the water incorporated in the polymer).

The chemical shift measures of $^{23}$Na and those carried out on the acetyl group of hyaluronic acid are aimed at determining whether the interaction between the two polymeric materials involves the polar ionized groups of the hyaluronic acid or its acetyl group.

The measures carried out on the anomeric protons are aimed at determining which types of TSP units are prevalently involved in the interaction with HA.

Samples Preparation for the NMR Analysis and Measurement Methods

The mother solutions were prepared dissolving solid polymers in $D_2O$ at the desired concentrations. Two series of solutions were prepared, the first one obtained after stirring at ambient temperature for 12 h and the second one after stirring for 12 h at ambient temperature and stirring under heating at 80° C. for about 60 min. The results obtained from the two series of solutions were completely overlapping; therefore in the following discussion no distinction will be made between them.

The NMR studies were carried out on a NMR Varian INOVA 600 14T spectrometer, operating at 600 MHz for $^1$H and 158.6 MHz for $^{23}$Na, provided by a 5 mm inverse triple-resonance probe and a 5 mm broadband probe for direct examination. The spectrometer is equipped with a temperature control system of ±0.1° C.

The selective proton relaxation times spin-spin $T_1$ are those obtained with the standard sequence inversion-recovery (180°-τ-90°-acquisition) for selective application of an impulse of inversion of the desired frequency.

The relaxation times spin-spin $T_2$ were measured using the sequence Carr-Purcell-Meiboom-Gill (CPMG) $(90°-\tau-(180°-2\tau)_n)$.

The DOSY maps (Diffusion Ordered SpectroscopY) were registered using a relaxation time of 3 s with a number of transients equal to 4. 30 gradients were utilized and the parameters δ e Δ were optimized (1 ms and 80 ms, respectively) to obtain a fall up to 10-5% of the initial signal.

Measurement of the Relaxation Time $$\left(R_2 = \frac{1}{T_2}\right)$$

of Water

First of all, measures were taken of the relaxation time $T_2$ of water in solutions containing the two pure polymers, with variable concentrations from 0.1% to 1%.

For TSP, values are measured increasing from 0.90 s$^{-1}$ in the most diluted solution (0.1% w/w) up to 3.08 s$^{-1}$ in the solution having the concentration of 1%. The increase of the relaxation speed spin-spin is according to what is expected based on the increase of the molar fraction of bonded water, which follows the increase of the polymer concentration.

For pure hyaluronic acid a similar increase of the relaxation parameter of water is noticed when increasing the concentration of polymer. Not only the measured values are remarkably lower in respect of what observed for TSP at the same concentration, but also the total variation is significantly lower. Taken into account that the molecular weights of the two polymers are both very high, the said difference may be reasonably correlated to the different tendency to self-aggregation of the two polymers: probably TSP has a bigger tendency to self-associate at increasing concentrations in respect of HA and as a consequence of the self-aggregation phenomena an increase of the bonded water fraction in respect of free water occurs.

Then, the relaxation speeds of water were measured in TSP-HA mixtures having a constant total concentration equal to 0.5% (solution c), but with variable rates between the two components. The measured values were compared with those obtained for the two pure polymers at the same concentration of the mixture or at its total concentration. The results obtained with varying weight ratios between TSP and HA allow to conclude that with ratios TSP/HA variable from 3:2 to 4:1 the interaction between the two polymeric materials becomes strongly cooperative, thus leading to a sudden increase of the molar fraction of bonded water in respect of that typical of the single polymers at the maximum concentration.

In the solutions having total concentration equal to 1% (solution d), the behaviour is reproduced, namely, for TSP/HA ratios comprised between 6.4 and 8.2, the relaxation speed of water in the mixture has a sudden increase up to a value which is bigger than the measured value for TSP and for HA, both at the same concentration in which each of them is present in the mixture and at the concentration corresponding to the total value (1%). The cooperating behaviour of the two polymers is therefore confirmed; this behaviour which seems to more critically depend on the ratio between the two polymers than on their total concentration.

Longitudinal Relaxation Speed Measurement $$\left(R_1 = \frac{1}{T_1}\right)$$

of the Acetyl Group of Hyaluronic Acid

The longitudinal relaxation speed $R_1$ of the acetyl protons of hyaluronic acid was measured in mixtures having a total constant concentration equal to 0.5% and variable TSP/HA ratios. The behaviour of the relaxation speed $R_1$ of the acetyl group is particularly interesting in mixtures HA/TSP having total concentration 0.5%, wherein it is observed once more a decrease of the relaxation speed $R_1$ with increasing HA concentration, but with absolute values that are still lower than those measured in the absence of TSP at the same concentration. The amount of the reduction produced in the relaxation speed in the acetyl group as a consequence of the presence of TSP became higher at variable ratios from 3:2 to 4:1; in this gap the remarkable synergistic effect of the two polymers is confirmed.

Also the relaxation speed spin-spin $R_2$ of the acetyl protons follows the same behaviour, both in the pure polymer and in its mixture with TSP; namely on increasing the HA concentration a decrease of the relaxation parameter is obtained, but the relaxation speeds in the mixture are lower, and the decrease in the mixture in respect of the pure component increases with high TSP/HA ratios.

Relaxation Speed Spin-Spin $R_2$ Measurement of Selected TSP Protons in Presence and Absence of Hyaluronic Acid at the Total Concentration of 0.5%.

In the spectrum of the mixtures, the anomeric protons of TSP at 5.06 ppm, 4.85 ppm and 4.45 ppm result to be not overlapped to signals of hyaluronic acid and, as such, they were taken as a base with the aim of obtaining information on the TSP protons involved in the interaction with HA.

In particular, the proton at 4.45 ppm corresponding to the units of Glucose and Galactose behaves in a completely different way with respect to the other protons. In fact, its value is scarcely dependent on the pure component solution concentration. The same changes in a significant way in presence of HA; in particular, differently from the other protons, it undergoes a significant decrease when the HA content increases. This behaviour must be ascribed to the conformational variations induced in TSP as a consequence of the interaction with HA.

Conclusions

The results of the NMR studies synthesized above clearly show that the interaction between TSP and HA becomes cooperative in dependence of the ratio by weight between the two polymers. Such interaction leads to conformational variations that mainly interest the internal units of glucose and galactose of TSP and the acetyl groups of HA. The carboxyl groups of HA itself, on the contrary, seem not to be influenced. The latter, probably, being present in ionic form, always tend to arrange themselves facing phase instead than TSP with which HA interacts. The latter conclusion is supported by the poor effect on the sodium chemical shift consequent to the variations of the total concentration and of the ratio between the two polymers.

The effect of the interaction on the ability of the two polymers to bond water is very important: this is more marked in the mixtures in respect of the pure polymers. The studies carried out have clearly shown the existence of an interval of TSP/HA ratio comprised between 3.2 and 4:1, wherein the ability of the mixtures to incorporate water becomes very high. Such property appears to be fundamental to the purposes of the adhesive and biocompatibility characteristics of the resulting polymeric mixture.

Evaluation of the Effectiveness of Mixtures of HA and TSP in an Animal Model, Compared to Preparation on the Market as Artificial Tear One of the assumptions for the application of artificial tears is a normal condition of the tear film. The eyes present more and more often problems of lachrymation, also due to the use of video-terminals, to the atmospheric pollution, to the alimentation and to the environmental allergies that affect the quality and quantity of the lachrymation and, consequently, the possibility of applying contact lenses. To this regard, it should be noticed that an alteration of the tear film inevitably leads to a definitive refuse of the therapy with artificial tears.

In view of the prolonged administration of a product for topic use such as artificial tears, it is particularly important to have tests available that may guarantee the absence of serious side effects, such as lens opacification and sufferance of the retina.

In the first section of the preclinical trials carried out, the effectiveness and the possible side effects of the proposed product according the invention were evaluated in comparison to other five other products already on the market on a healthy animal model; the second section, instead, exploits a suitable pathologic model to more thoroughly investigate the real advantages involved in the treatment with artificial tears.

Lachrymation Test

The Schirmer I test involves the introduction of a bibula paper strip, of standard material and size, in the inferior conjunctival fornix, towards the external canthus. The strip is left in situ for a predetermined period of time (3 min) and after said period the soaked part is measured, excluding the folded portion. The time employed by the tear fluid to ascend and the length in mm of the paper portion soaked by the tears provides the size of the tear secretion.

In the daily practice, it is possible to carry out the test for a time period of 1 min. and multiply by 3 the obtained value. Then the result—being less affected by reflex lacrhymation—is compared with the values defined by Schrimer. A soaked portion of less than 5 mm (in 5 minutes) is considered pathological.

The pH evaluation, that is carried out by the use of suitable turnsole paper, is an important test to reveal any pathologic changes in the epithelium. The normal values of the tears pH in man range between 6.8 and 7.4, while in the rat the said range moves towards higher values (from 7 to 8). However, in a pathological status, the tear fluid becomes basic.

The Ferning test was described in its generalities in the introductive section.

The corneal examination comprises the marking with sodium fluorescein, after which the corneal surface is examined with fluorescence microscope. A maculate marking reveals the presence of dry zones on the ocular surface, symptom of corneal dryness. The marking with Lissamine Green, instead, allows to reveal the presence of ulcerated or necrotic zones on the ocular surface.

Esecution of the Experiments

The experimentation included the setting up of the following experimental groups, each one composed by 3 albino rats (=6 eyes).
1. control group
2. composition according to the invention (0.4% hyaluronic acid+0.2% TSP): (TSP+HA)
3. mixture of glycols and hydroxypropyl-guar (Systane multidose bottle, Al-con): (Guar Gum)
4. 0.15% hyaluronic acid (Blu Yal monodose, Sooft): (HA 0.15%)
5. 0.4% hyaluronic acid (Dropstar monodose, Farmigea): (HA 0.4%)
6. galactoxyloglucan (TSP 0.2% monodose, Farmigea): (TSP 0.2%)
7. 0.5% sodium carboxymethylcellulose (Celluvisc monodose, Allergan): (CMC 0.5%)
8. 0.2% hyaluronic acid (Hyalistil 0.2%, Sifi): (HA 0.2%)

Phase 1

During the first experimental phase, the quality of the products on a model of healthy animals was evaluated; the animals were treated with the respective solutions 3 times per day for 5 days. Tests were carried out with the following modalities.

The Schirmer I test was carried out after 2, 3, 4, and 5 days, after atropine administration, in both eyes of all the animals, maintaining for 3 min. the bibula paper strips in the external tertium of the conjunctival fornix. The pH measurement was carried out the day 0 and the day 5 using the suitable turnsole paper. The Ferning test was carried out on samples of tear film from the treated animals with the different formulations at the day 5, mixing 10 µl of each formulation with 2 µl of artificial tears. The mixture was examined with a microscope, at room temperature (20±1° C.). The corneal examination was carried out after 3, 4 and 5 days, after administration of atropine. After marking with fluorescein and with Lissamine Green, the corneal surface was observed using a lamp with suitable filters.

The Schrimer test results did not show any quantitative differences in the tear volume upon treatment of the animals with the composition of the invention and with the other products already available on the market. Also the evaluation of the tear pH did not show any pathological variations either for the product according to the invention or for anyone of the other products under examination. Neither the corneal examination after marking with fluorescein and with Lissamine Green showed any pathological alterations of the cornea after the treatment with the product according to the invention, analogously to what observed for the other substances available on the market. The ferning tests produced images of the crystallized tears which do not show essential differences between the various treatments under comparison.

Therefore, the tests of the Phase 1 showed the absence of negative interactions between the proposed composition and the physiological status of the conjunctiva-cornea, in the same way as other artificial tear formulations already on the market.

Phase 2

In this experimental phase different possible animal models were evaluated, and a model of dry eye in the albino rat was set up, which involves the use of three cycles of 2.5 h composed as follows:

T0 (0 min): intraperitoneal injection of 4 mg/kg atropine and topical application of 1% atropine
T1 (40 min): Anesthesia with 8.5% chloral hydrate and exposure to a continuous and constant flow of dry air for 1 h.
T2 (100 min): End of the air flow.
T3 (130 min): 1% Topical atropine
T4 (150 min): End of the cycle.

The animals treated with the tears under study received one topical administration of the formulations after 30 min. from T0 and at T2.

The Schirmer test evaluation shows hyperlachrymation at the end of the three cycles, as a response mainly of inflammatory-exudative type. Even if it is impossible to detect significant differences because of the high variability found among the animals, a reduced trend due to the composition (TSP+HA) according to the invention and to the 0.5% TSP is evident. The latter points to a better protection from the harmful stimulations. The tear pH evaluation did not show any pathological changes after three cycles for any one of the experimental groups.

In regard of the ferning test, although no significant differences between groups under test where detected, it is possible to confirm the presence of protective properties in some products, including the composition of the invention, in comparison with the control group.

The result of the corneal test with fluorescein and Lissamine Green, evaluated as percent of the corneal surface interested by the ulcerous or necrotic lesion, showed a protection similar in the various formulations from the damage induced by the execution of the three cycles described above.

In conclusion, the tests reported above have evidenced not only the absence of negative interactions between the composition according to the invention and the physiological status of conjunctiva-cornea (Phase 1), but also a better recovery from the histo-physiological damages following a strong reduction of lachrymation. The said tests allow to establish that the proposed combination shows the suitable features for its valid use as artificial tear and in the treatment of the dry eye syndrome.

Pilot Clinical Study on the Effectiveness of Mixtures of a Combination of 0.2% TSP and 0.4% HA in the Dry Eye Syndrome Treatment In order to evaluate the effectiveness of a combination of TSP and HA in the treatment of the dry eye syndrome a preliminary clinical trial was carried out on twenty-one (21) subjects of both sexes (42 eyes). The criteria of inclusion in the experiment were the absence of ocular infections, the absence of any ocular pathology different from dry eye (with the exception of refractive alterations) and the absence of use of contact lenses.

The test consisted in a controlled randomized open study on three parallel groups, with blind evaluation, without the wash out step, wherein the products administered as artificial tear were the following:

Study group: Mixture of equal weight proportions of TSP ophthalmic solution (TSP 0.2%) and HA ophthalmic solution (HA 0.4%), referred to below as "TSP+HA";
$1^{st}$ control group: ophthalmic solution 0.2% TSP (TSP, Farmigea), referred to below as "TSP";
$2^{nd}$ control group: ophthalmic solution 0.4% HA (Dropstar, Farmigea), referred to below as "HA".

At the time of the randomization, the patients were instructed by the oculist to provide the self-instillation, two drops twice per day directly into the conjunctival sac, of each of the three above products in comparison.

As primary end-point of test the score variation of the conjunctival microvilli number from the beginning and end of the treatment was determined. As secondary end points, the score variation of the subjective symptomatology, of the objective symptomatology, of the conjunctival cytological pattern (scraping), of the composite score (as defined below) and of the tolerability and safety of the product were determined.

The evaluations of the subjective symptomatology, of the objective symptomatology, of the tolerability and safety were carried out in open, while the evaluation of the conjunctival cytology and of the microvilli were carried out in blind, by an observer ignoring the treatment associated to each subject.

The total duration of the treatment was 60 days (±8 days) for all three patients groups.

Evaluations

Microvilli evaluation—The effects of the treatment on the microvilli were evaluated with scanning electron microscopy (SEM). For each eye exam-fined repere points using the vascular grid were identified, in order to operate the basal and final withdrawals in the same area. A sample of epithelium was taken, separately for each eye, from the superior temporal bulbar conjunctiva using the "impression cytology" technique.

The withdrawal was carried out from a minimum of 48 hours to a maximum of 7 days after the ophthalmoscopic exam. In the same session when the sample was taken for the microvilli study, a few minutes before, a conjunctival scraping was carried out for the cytological evaluation.

The samples were then treated and fixed for an exam with SEM and measured using a scale of 4 points (from 1 to 4).

Subjective symptomatoloqy—This was the first of the parameters evaluated during each visit (basal or final), when the patient was invited to refer the subjective degree of nuisance suffered during the last week for the following ocular symptoms: itching, burning sensation, irritation, lachrymation. Based on the direct information provided by the patient, the physician of the experimentation converted the total intensity of the ocular discomfort over an analogical scale of 4 points (from 1 to 4), wherein the degree 1 represented the symptom absence, the degree 2 a light symptomatology, the degree 3 a moderate symptomatology and the degree 4 represented the most severe symptomatology Objective symptomatology—The epithelial sufferance and the possible extension of the kerato-conjunctival lesions was determined after the subjective evaluation. It was been evaluated by the oculist, after the determination of the subjective symptomatology, with a slit lamp and fluorescein and measured with an analogical scale of 4 points (from 1 to 4) based on the following criteria: degree 1, epithelial sufferance absent or limited to only a quadrant; degree 2, epithelial sufferance limited to two quadrants; degree 3, epithelial sufferance that clearly affecting two quadrants with further signals of sufferance in the other quadrants; degree 4 the epithelial sufferance is extended to the whole ocular surface.

Conjunctival cytology—the inflammatory cellular component was taken from the conjunctiva with scraping and without anaesthetic, fixed with May-Grunwald solution (methylene blue eosinate) found on the market.

The scraping was carried out from 2 and 7 days after the ophthalmoscopic examination, during the same session when the withdrawal of the sample for the microvilli study was scheduled.

The slide was coloured in the laboratory and observed with an optical microscope. The evaluation was carried out in blind based on a scale of 4 points: 1=only epithelial cells and/or lymphocytes (+); 2=lymphocytes (+), neutrophyles (+); 3=lymphocytes (++), neutrophyles (++); 4=lymphocytes (++), neutrophyles (++) and/or eosinophyles (+).

Composite score—it represents the sum of the four parameters described above and it was evaluated as a surrogated index of a global effectiveness.

Safety and tolerability—Safety and tolerability of the products object of the study were determined with direct questions from the physician to the patient.

Effects on Microvilli

As noted, the effects of the treatment on the microvilli photographed with scanning electron microscopy were determined evaluating with a 4-points scale. Before randomization, the three groups were quite homogeneous, the group "TSP" having an average score of 3.0, and the groups "TSP+HA" and "HA", having an average score of 3.3. Also the dispersion of the data appeared moderate, being the variation coefficient of 26% vs 22% vs 22%, respectively for TSP, TSP+HA, HA.

TABLE 1

| Microvilli - Pre-post comparison on the average values | | | | | |
|---|---|---|---|---|---|
| MTSP | | TSP + HA | | HA | |
| Basal | Day 60 | Basal | Day 60 | Basal | Day 60 |
| N | 14 | 14 | 14 | 14 | 14 | 14 |
| Min | 2 | 1 | 2 | 1 | 2 | 2 |
| Max | 4 | 4 | 4 | 3 | 4 | 4 |
| Average | 3.0 | 2.7 | 3.3 | 1.4 | 3.3 | 3.0 |
| St. Dev. | 0.8 | 0.9 | 0.7 | 0.6 | 0.7 | 0.8 |

TABLE 1-continued

| Microvilli - Pre-post comparison on the average values | | | | | |
|---|---|---|---|---|---|
| MTSP | | TSP + HA | | HA | |
| Basal | Day 60 | Basal | Day 60 | Basal | Day 60 |
| Var. Coeff. | 0.26 | 0.34 | 0.22 | 0.45 | 0.22 | 0.26 |
| p (Wilcoxon) | 0.602 | | <0.0001 | | 0.219 | |

Figure 1:
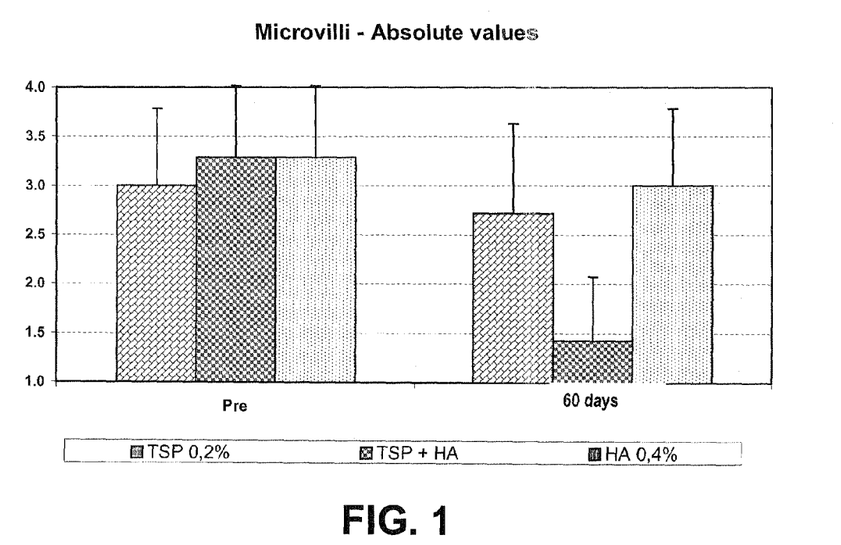
FIG. 1 shows, in form of histogram, the results of a pilot study on the effectiveness of the composition according to the invention in the treatment of dry eye syndrome, as concerns the evaluation of the conjunctival microvilli, in terms of absolute values.
Figure 2:
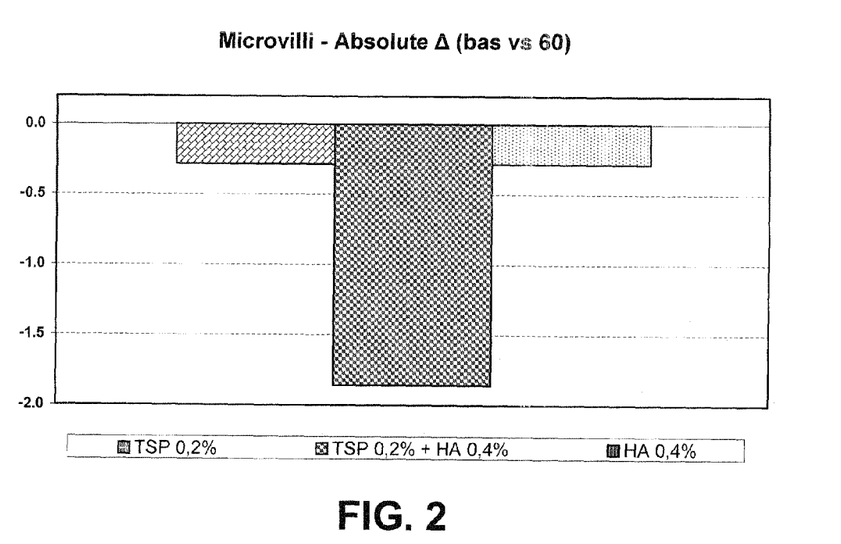
FIG. 2 shows the results, in the same pilot study, of the evaluation of the conjunctival microvilli, in terms of variation of the basal values.

As illustrated in Table 1 and in the histograms of FIGS. 1 and 2, after 60 days of treatment in the group TSP, a slight improvement of the number of conjunctival microvilli (−0.3 points) was observed, equal to −9.5% in respect of the basal value (NS in the Wilcoxon test). Similarly, the behaviour in the group treated with HA wherein, after 60 days, an average improvement of 0.3 points was observed, equal to −8.7% in respect of the basal value (NS in the Wilcoxon test).

In the group treated with TSP+HA it was observed, instead, an average improvement over 5 times higher, with a score that moved towards normality of 1.9 points, equal to a percent improvement of 56.5% in respect of the basal value ($p<0.0001$ in the Wilcoxon test).

As shown in the following Table 2, differently from what occurred for the eyes treated with TSP only or with only HA, all the 14 eyes treated with TSP+HA have had, after 60 days, a score improvement (from 1 to 3 points).

TABLE 2

| | TSP 0.2% | | TSP 0.2%/ HA 0.4% | | HA 0.4% | |
|---|---|---|---|---|---|---|
| 3 | 0 | 0.0% | 0 | 0.0% | 0 | 0.0% |
| 2 | 1 | 7.1% | 0 | 0.0% | 0 | 0.0% |
| 1 | 2 | 14.3% | 0 | 0.0% | 1 | 7.1% |
| 0 | 5 | 35.7% | 0 | 0.0 | 8 | 57.1% |
| −1 | 4 | 28.6% | 6 | 42.9% | 5 | 35.7% |
| −2 | 2 | 14.3% | 4 | 28.6% | 0 | 0.0% |
| −3 | 0 | 0.0% | 4 | 28.6% | 0 | 0.0% |

For the statistic analysis, the Kruskal-Wallis significance test was applied on the absolute values of the differences between the basal and final observations. Although the number of the examined samples was relatively limited, the analysis showed a difference statistically very significant in the treatment groups ($p<0.0001$).

Figure 3:
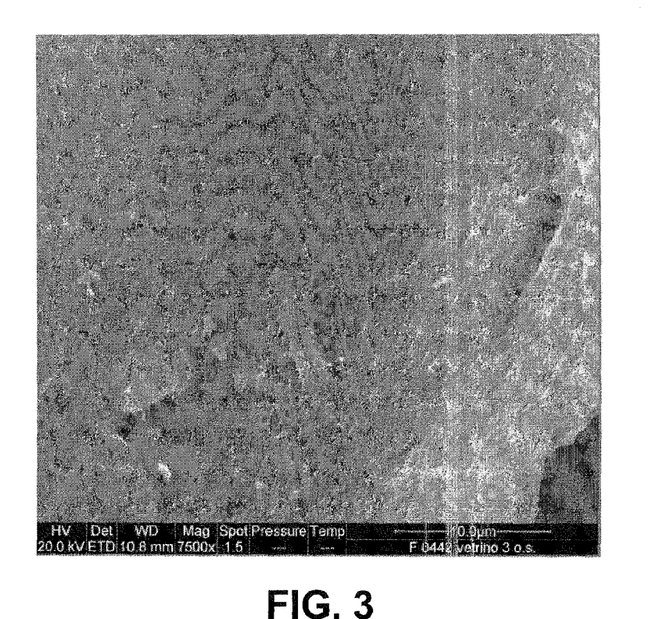
FIG. 3 shows a SEM 7500× image of a left eye conjunctival epithelium of a female patient of the same pilot study, said patient belonging to the group TSP+HA, before the treatment.
Figure 4:
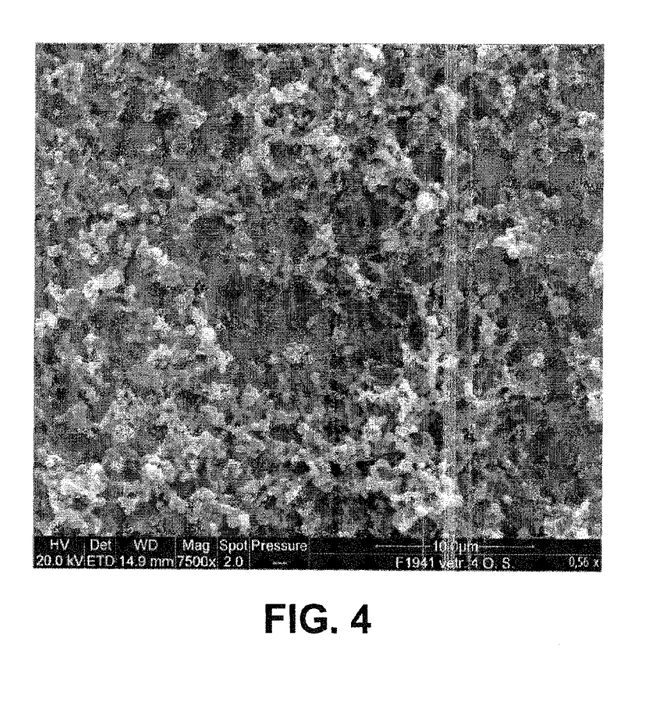
FIG. 4 shows a SEM 7500× image of a left eye conjunctival epithelium of the same female patient of FIG. 3, after 60 days of treatment with TSP+HA.

The attached FIGS. 3 and 4 show, using a scanning electron microscope, the development of the microvilli presence on the conjunctival epithelium in a female patient aged 64 treated for 60 days with TSP+HA. FIG. 3 allows to appreciate a glabrus epithelial surface due to the almost complete absence of microvilli, based on the criteria described before, to this histological frame a score of 4 (maximal reduction of the microvilli presence) had been assigned. In the same patient and in the same zone of the conjunctiva of the same eye, FIG. 4 shows a rich vegetation of microvilli, which allow to assign to this frame a score of 1, substantially typical of a normal condition.

As pointed out in Table 2, in the group treated with TSP+HA, 4 eyes (28.6%), in 3 subjects, showed an improvement of the microvilli score equal to 3, while the same number of eyes showed an improvement in the score equal to 2 points. Six eyes (42.9%) showed an improvement in the score equal to only one point.

Effects on the Subjective Symptomatology

The intensity of the subjective symptomatology was determined with analogical scale of 4 points under the form of intensity of the ocular nuisance, as described above. At the basal value, the three groups presented relative homogeneity, both from the point of view of the absolute values of the scores (with an average maximum gap of 0.3 points), and as dispersion values measured under the form of variation coefficient (33% vs 12% vs 29%, respectively for TSP, TSP+HA and HA).

TABLE 3

Subjective symptomatology - Pre-post comparison on average values

|  | TSP | | TSP + HA | | HA | |
| --- | --- | --- | --- | --- | --- | --- |
|  | Basal | Day 60 | Basal | Day 60 | Basal | Day 60 |
| N | 14 | 14 | 14 | 14 | 14 | 14 |
| Min | 1 | 1 | 2 | 1 | 1 | 2 |
| Max | 4 | 4 | 3 | 4 | 4 | 4 |
| Average | 2.6 | 2.6 | 2.9 | 1.9 | 2.8 | 2.6 |
| St. Dev. | 0.9 | 0.9 | 0.4 | 1.1 | 0.8 | 0.6 |
| Var. Coeff. | 0.33 | 0.33 | 0.13 | 0.59 | 0.29 | 0.25 |
| p (Wilcoxon) | 1.000 | | 0.014 | | 0.375 | |

Figure 5:
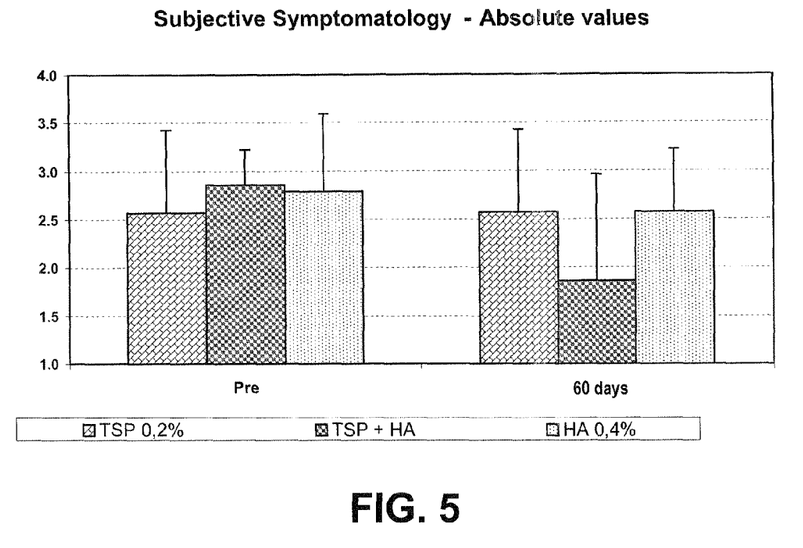
FIG. 5 shows in form of histogram the results of the same pilot study of FIG. 1, as concerns the evaluation of the effects on the subjective symptomatology, in terms of absolute values.
Figure 6:
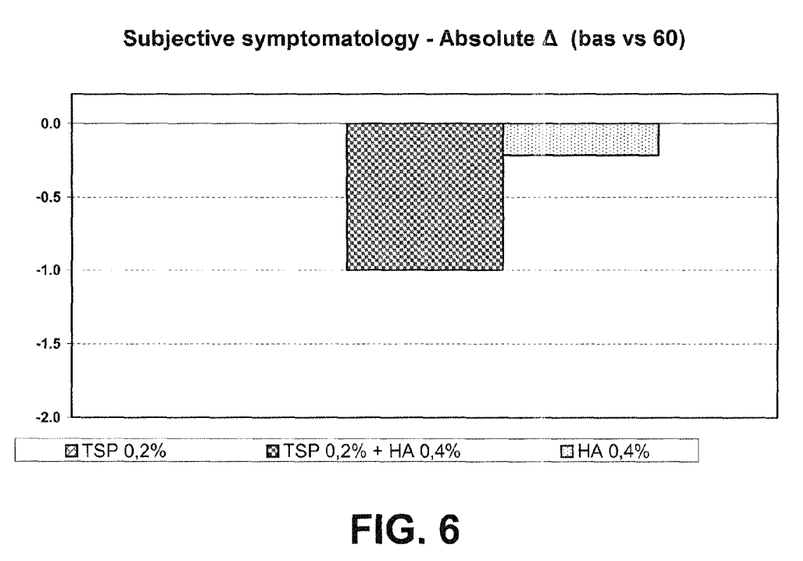
FIG. 6 shows the results, in the pilot study, of the evaluation of the effects of subjective symptomatology, in terms of basal values.

After 60 days of treatment, as illustrated in the histograms of FIGS. 5 and 6, no variation of the subjective symptomatology was observed in the TSP group, with a score that remained at the value of 2.6, while in the group treated with HA a light improvement was observed, not statistically relevant, equal to −0.2 point of the average score (−7.7%).

The improvement of the group treated with TSP+HA, were sensibly more evident, and statistically relevant in the Wilcoxon test, showing an average score reduced of 1.0 point, equal to the 35.0% in respect to the basal value.

As it is shown in the following Table 4, only two eyes of the 14 under treatment with TSP+HA showed a score worsening of the subjective symptomatology and one remained without variation, while for 6 and 5 eyes improvements were registered, respectively of 1 and 2 points.

TABLE 4

|  | TSP 0.2% | | TSP 0.2%/ HA 0.4% | | HA 0.4% | |
| --- | --- | --- | --- | --- | --- | --- |
| 3 | 0 | 0.0% | 0 | 0.0% | 0 | 0.0% |
| 2 | 0 | 0.0% | 0 | 0.0% | 0 | 0.0% |
| 1 | 3 | 21.4% | 2 | 14.3% | 1 | 7.1% |
| 0 | 8 | 57.1% | 1 | 7.1% | 9 | 64.3% |
| −1 | 3 | 21.4% | 6 | 42.9% | 4 | 28.6% |
| −2 | 0 | 0.0% | 5 | 35.7% | 0 | 0.0% |
| −3 | 0 | 0.0% | 0 | 0.0% | 0 | 0.0% |

The statistic analysis was carried out applying the Kruskal-Wallis test to the absolute values of the differences between the basal and the final observations and it showed a statistically significant difference between the three groups (p=0.005).

Effects on the Objective Symptomatology

The objective symptomatology was measured with a 4 points scale evaluating the degree of affection of the 4 corneal-conjunctival sectors using a slit lamp as described above. In the basal values, the three groups presented a small degree of non-homogeneity, not statistically relevant, being the group TSP+HA at an average score of 2.8, higher of 0.3 point than the score of the TSP group and of 0.1 point of the score of the HA group. The data dispersion results relatively high for all the three groups, with a variation coefficient of 41% vs 29% vs 34%, respectively for TSP, TSP+HA, HA.

TABLE 5

Objective symptomatology - Pre-post comparison on the average values

|  | TSP | | TSP + HA | | HA | |
| --- | --- | --- | --- | --- | --- | --- |
|  | Basal | Day 60 | Basal | Day 60 | Basal | Day 60 |
| N | 14 | 14 | 14 | 14 | 14 | 14 |
| Min | 1 | 1 | 1 | 1 | 1 | 1 |
| Max | 4 | 4 | 4 | 3 | 4 | 4 |
| Average | 2.5 | 2.2 | 2.8 | 1.9 | 2.7 | 2.6 |
| St. Dev. | 1.0 | 1.0 | 0.8 | 0.8 | 0.9 | 0.8 |
| Coeff. Var. | 0.41 | 0.44 | 0.29 | 0.41 | 0.34 | 0.29 |
| p (Wilcoxon) | 0.125 | | 0.006 | | 0.347 | |

Figure 7:
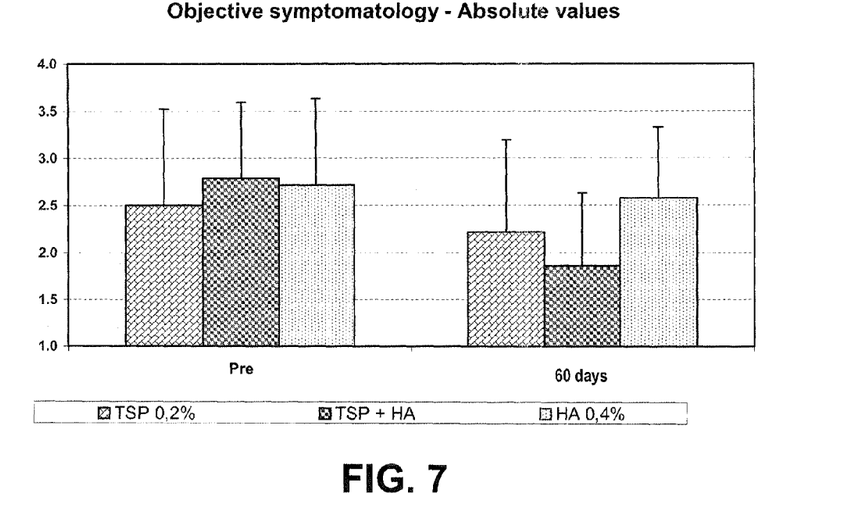
FIG. 7 shows, in form of histogram, the results of the same pilot study of FIG. 1, as concerns the evaluation of the effects on the objective symptomatology, in terms of absolute values.
Figure 8:
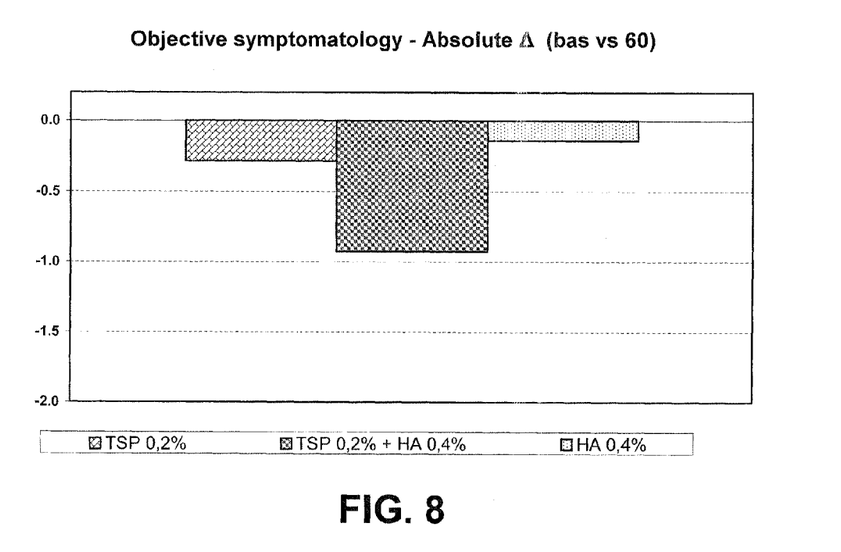
FIG. 8 shows the results, in the same pilot study, of the evaluations of the effects of subjective symptomatology, in terms of basal values.

As it is better shown in the histograms of FIGS. 7 and 8, as well as in Table 5, after 60 days of treatment, a slight improvement of the objective symptomatology (−0.3 points), equal to 11.4% in respect of the basal value was observed in the TSP group. The progress in the group treated with HA was smaller, this group showing, after 60 days, a reduction of the average score equal to −0.1 point (−5.3%). In both cases, the differences were not statistically relevant to the Wilcoxon test.

In the group treated with TSP+HA, instead, after 60 days of treatment, the lowest average score was observed, with 1.9, although the starting point was slightly higher basal values. This is equivalent to an improvement of −0.9 points, statistically relevant, which represented a variation of 33.3% in respect of the basal value.

As it is shown in the following Table 6, only one of the 14 eyes treated with TSP+HA had a worsening in the score of the objective symptomatology, one remained without variation and 12 had an improvement.

TABLE 6

|  | TSP 0.2% | | TSP 0.2%/ HA 0.4% | | HA 0.4% | |
| --- | --- | --- | --- | --- | --- | --- |
| 3 | 0 | 0.0% | 0 | 0.0% | 0 | 0.0% |
| 2 | 0 | 0.0% | 0 | 0.0% | 1 | 7.1% |
| 1 | 0 | 0.0% | 1 | 7.1% | 0 | 0.0% |
| 0 | 10 | 71.4% | 1 | 7.1% | 9 | 64.3% |
| −1 | 4 | 28.6% | 10 | 71.4% | 4 | 28.6% |
| −2 | 0 | 0.0% | 2 | 14.3% | 0 | 0.0% |
| −3 | 0 | 0.0% | 0 | 0.0% | 0 | 0.0% |

The statistic analysis was carried out applying the Kruskal-Wallis test to the absolute values of the differences between the basal and the final observations. In regard to the objective symptomatology it is possible to confirm that the differences observed in the three groups of the patients are statistically relevant (p=0.02).

Effects on Cytology

The presence of inflammatory cells was evaluated with a scale of 4 points, according to what described above. In the basal values, before the randomization, the three groups were very inhomogeneous, even if not in a statistically relevant way. In fact, in the HA group, which was the least serious, an average score of 1.9 was determined, in the TSP group the score was 2.1, and in the TSP+HA group, the most serious, the average score of 2.7 was detected, with a gap between the extremes of 0.8. Also the data dispersion appeared sensible with a variation coefficient of 44% vs 37% vs 55%, respectively for TSP, TSP+HA, HA.

TABLE 7

Cytology - Pre-post comparison on the average values

|  | TSP | | TSP + HA | | HA | |
| --- | --- | --- | --- | --- | --- | --- |
|  | Basal | Day 60 | Basal | Day 60 | Basal | Day 60 |
| N | 14 | 14 | 14 | 14 | 14 | 14 |
| Min | 1 | 1 | 1 | 1 | 1 | 1 |
| Max | 4 | 3 | 4 | 3 | 4 | 3 |
| Average | 2.1 | 2.3 | 2.7 | 1.9 | 1.9 | 2.0 |
| St. Dev. | 0.9 | 0.9 | 1.0 | 0.8 | 1.0 | 0.6 |
| Coeff. Var. | 0.44 | 0.40 | 0.37 | 0.43 | 0.55 | 0.28 |
| P (Wilcoxon) | 0.688 | | 0.094 | | 1.000 | |

Figure 9:
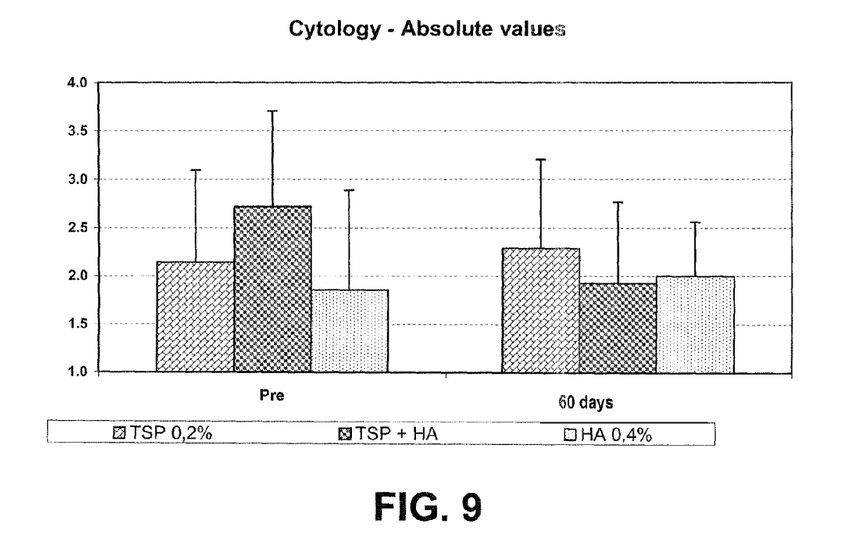
FIG. 9 shows, in form of histogram, the results of the same pilot study of FIG. 1, as concerns the evaluation of the effect on the cytology, in terms of absolute values.
Figure 10:
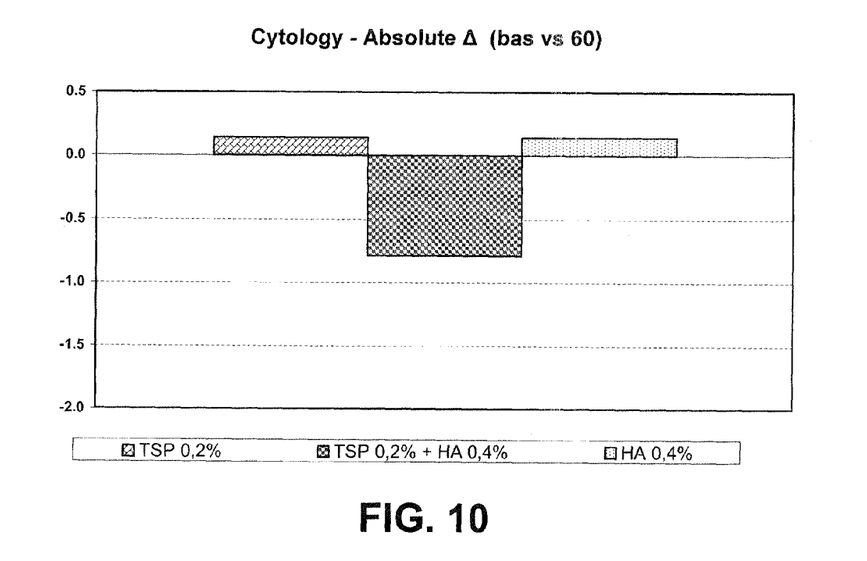
FIG. 10 shows the results, in the same pilot study, of the evaluation of the effects on the cytology, in terms of variation in respect of the basal values.

Table 7 and the attached FIGS. 9 and 10 show that, after 60 days of treatment both in the TSP group and the HA group, a slight worsening of the cytologic profile was observed. On the contrary, in the group treated with TSP+HA a strong improvement in the cytologic profile was observed, even if not statistically relevant, with a passage of the average score of 2.7 to a value of 1.9, with a percent improvement of 28.9% in respect of the basal value.

As it is shown in the following Table 8, 7 eyes on the 14 treated with TSP+HA have shown an improvement in the score, after 60 days, while 6 remained unaltered, and one had worsened.

TABLE 8

|  | TSP 0.2% | | TSP 0.2%/HA 0.4% | | HA 0.4% | |
| --- | --- | --- | --- | --- | --- | --- |
| 3 | 0 | 0.0% | 0 | 0.0% | 0 | 0.0% |
| 2 | 0 | 0.0% | 0 | 0.0% | 0 | 0.0% |
| 1 | 4 | 28.6% | 1 | 7.1% | 5 | 35.7% |
| 0 | 8 | 57.1% | 6 | 42.9% | 6 | 42.9% |
| −1 | 2 | 14.3% | 4 | 28.6% | 3 | 21.4% |
| −2 | 0 | 0.0% | 1 | 7.1% | 0 | 0.0% |
| −3 | 0 | 0.0% | 2 | 14.3% | 0 | 0.0% |

Analogously to the other parameters, for the statistic analysis the significance Kruskal-Wallis test was applied on the absolute values of the differences between the basal and final observations. This analysis evidenced a statistically relevant difference between the groups (p=0.031).

Composite Score

As noted, the composite score represents the sum of the four parameters described above (microvilli, subjective symptomatology, objective symptomatology, cytology) and it is a surrogated index of the global effectiveness. Its maximum theoretical value is 16. In spite of the source of possible off-balance between the groups, mainly due to the cytology, after randomization, at the basal value, the three groups were sufficiently homogeneous, as it results from the following Table.

TABLE 9

Total Score - Pre-Post comparison on the average values

|  | TSP | | TSP + HA | | HA | |
| --- | --- | --- | --- | --- | --- | --- |
|  | Basal | Day 60 | Basal | Day 60 | Basal | Day 60 |
| N | 14 | 14 | 14 | 14 | 14 | 14 |
| Min | 6 | 4 | 8 | 4 | 5 | 6 |
| Max | 16 | 13 | 14 | 11 | 15 | 14 |
| Average | 10.2 | 9.8 | 11.6 | 7.1 | 10.6 | 10.1 |
| St. Dev. | 2.8 | 2.8 | 2.0 | 2.3 | 2.7 | 2.2 |

TABLE 9-continued

Total Score - Pre-Post comparison on the average values

|  | TSP | | TSP + HA | | HA | |
| --- | --- | --- | --- | --- | --- | --- |
|  | Basal | Day 60 | Basal | Day 60 | Basal | Day 60 |
| Coeff. Var. | 0.27 | 0.29 | 0.17 | 0.32 | 0.26 | 0.21 |
| P (Wilcoxon) | 0.555 | | <0.0001 | | 0.197 | |

Figure 11:
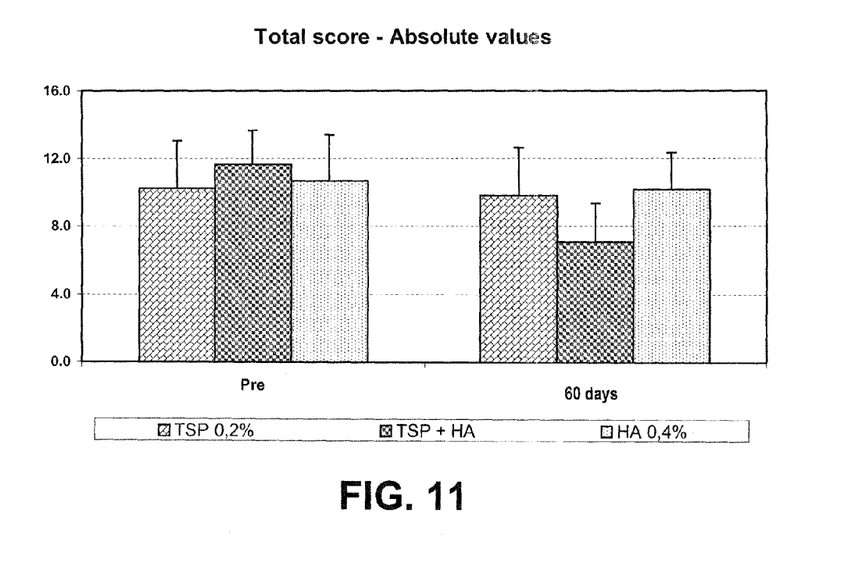
FIG. 11 shows, in form of histogram, the results of the same pilot study of FIG. 1, as concerns the total score (combined score) of the previous evaluation, in terms of absolute values.
Figure 12:
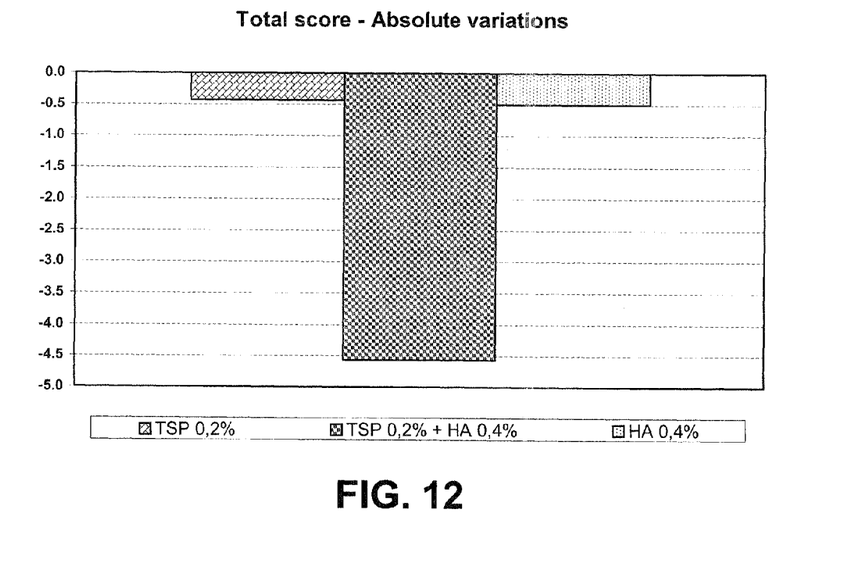
FIG. 12 shows the results, in the same pilot study, of the combined score of the previous evaluations, in terms of variation in respect to the basal values.

After 60 days of treatment, as it is shown in FIGS. 11 and 12, in the TSP group substantial variations vs. the basal were not detected. Analogous behaviour was noted in the group treated with HA, wherein, after 60 days, an improvement of 0.5 point occurred, equal to −4.7% in respect of the basal value (NS).

The improvement observed in the group treated with TSP+HA was about 10 times higher and statistically highly relevant, with −4.5 points equal to 39.3% in respect of the basal value. The improvement was highly significant to the Wilcoxon test.

Also for the composite score, for the statistic analysis the Kruskal-Wallis test was applied on the absolute values of the differences between the basal and final observations, which resulted as highly significant (p<0.0001).

Safety and Tolerability

In no treatment used in the pilot study described any problems linked to the tolerability or to the local or systemic safety were reported, with the exception of rare feedback related to a transitory misty vision associated to the products instillation and which normally lasted for a few minutes. Such effects, known also in respect of other tear substitutes, did not show differences in the three groups.

Conclusions

Based on the results of the study, it is possible to conclude that sufficient clinical evidences exist, also supported by evaluations carried out with scanning electronic microscopy, that the combination of TSP and hyaluronic acid in the same ophthalmic product produces a synergetic effect, showing results not obtainable when the two products are individually administered.

Such microscopic evidences indicate that at the base of the synergetic effect there is a rapid improvement of the condition of the conjunctival epithelium which, exposed to HA and TSP in combination, results as a microvilli regeneration. In their turn, the effects on the conjunctival epithelium produce an improvement of the subjective and objective symptoms which characterize the dry eye syndrome.

The present invention has been disclosed with particular reference to some specific embodiments thereof, but it should be understood that modifications and changes may be made by the persons skilled in the art without departing from the scope of the invention as defined in the appended claims.

The invention claimed is:

1. An ophthalmic preparation comprising from 0.05 to 2% by weight of tamarind seed polysaccharide and from 0.05 to 1% by weight of hyaluronic acid and an ophthalmically acceptable carrier.

2. The ophthalmic preparation according to claim 1, comprising from 0.1 to 1% by weight of tamarind seed polysaccharide and from 0.1 to 0.5% by weight of hyaluronic acid.

3. The ophthalmic preparation according to claim 1, wherein said tamarind seed polysaccharide has a molecular weight comprised in the range of 450,000 Da to 750,000 Da.

4. The ophthalmic preparation according to claim 1, wherein said hyaluronic acid has a molecular weight comprised in the range of 600,000 Da to 1,000,000 Da.

5. The ophthalmic preparation according to claim 1, comprising in aqueous solution 0.2% by weight of tamarind seed polysaccharide and 0.4% by weight of hyaluronic acid.

6. The ophthalmic preparation according to claim 1, further comprising one or more tonicity regulator agents.

7. The ophthalmic preparation according to claim 1, further comprising one or more ophthalmically acceptable acid(s) or base(s), as pH correctors.

8. The ophthalmic preparation according to claim 1, further comprising one or more buffers.

9. The ophthalmic preparation according to claim 1, further comprising one or more preservative agents.

10. The ophthalmic preparation according to claim 1, further comprising one or more chelating agents.

11. A method of producing a tear substitute comprising, combining tamarind seed polysaccharide and hyaluronic acid, water and one or more tonicity agents.

12. A method of treating dry eye syndrome comprising administering the ophthalmic preparation of claim 1.

13. The method according to claim 12, wherein said preparation comprises from 0.1 to 1% by weight of tamarind seed polysaccharide and from 0.1 to 0.5% by weight of hyaluronic acid.

14. The method according to claim 12 wherein said tamarind seed polysaccharide has a molecular weight comprised in the range of 450,000 Da to 750,000 Da.

15. The method according to claim 12 wherein said hyaluronic acid has a molecular weight comprised in the range of 600,000 Da to 1,000,000 Da.

\* \* \* \* \*